Figure 1:
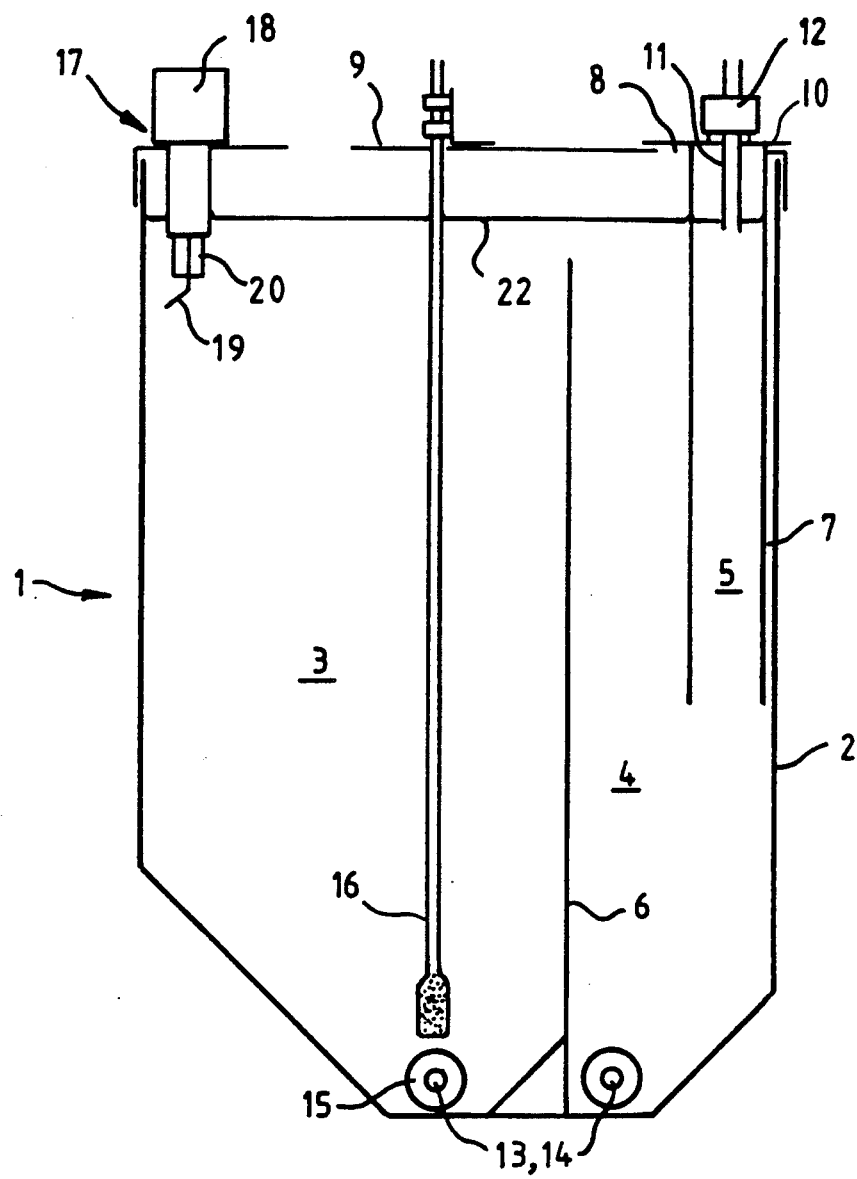

United States Patent [19]

Reid et al.

[11] Patent Number: 5,057,213
[45] Date of Patent: Oct. 15, 1991

[54] APPARATUS AND A SYSTEM FOR MONITORING IMPURITY IN A LIQUID

[75] Inventors: John M. C. Reid, Crowborough; Robert B. Nason, Barnehurst; David F. James, Hornchurch, all of England

[73] Assignee: Thames Water PLC, United Kingdom

[21] Appl. No.: 422,508

[22] Filed: Oct. 17, 1989

[30] Foreign Application Priority Data

Oct. 17, 1988 [GB] United Kingdom ............... 8824286

[51] Int. Cl.$^5$ ............................................. C02F 11/02
[52] U.S. Cl. ................................. 210/94; 210/96.1; 210/143; 210/220; 210/258
[58] Field of Search ............... 210/614, 746, 96.1, 210/44, 141, 143, 200, 201, 205-208, 218-220, 258

[56] References Cited

U.S. PATENT DOCUMENTS

| | | | |
|---|---|---|---|
| 3,983,031 | 9/1976 | Kirk | 210/614 |
| 4,329,232 | 5/1982 | McKenna | 210/614 |
| 4,564,453 | 1/1986 | Coplot et al. | 210/614 |
| 4,818,408 | 4/1989 | Hamamoto | 210/614 |

Primary Examiner—Tom Wyse
Attorney, Agent, or Firm—Rothwell, Figg, Ernst & Kurz

[57] ABSTRACT

Apparatus 1 for monitoring impurity in a liquid, specifically toxin(s) in activated sewage sludge, comprises a vessel 2 with a plurality of chambers 3 and 4 through which the liquid (sludge) is circulated in use to promote mixing, and a compartment 5 in the vessel in fluid communication with the chambers 3 and 4 and adapted to promote a quiescent settlement zone from which liquid is removable.

10 Claims, 2 Drawing Sheets

APPARATUS AND A SYSTEM FOR MONITORING IMPURITY IN A LIQUID

The invention relates to apparatus, and a system, for monitoring impurity in a liquid, particularly the presence of toxins in activated sewage sludge. The activated sludge process is prone to poisoning by a number of agents, the first indication of which may often be the sudden and complete loss of nitrification, in a sewage treatment works, with all of its associated hazards such as fish kills and the placing of an unacceptably high ammonia load on any watercourse receiving the works' effluent. Thus illegal discharge of cyanides/plating compounds in trade effluent can poison nitrifying organisms in the sewage sludge, so that nitrification is ceased and an unacceptably high level of nitrogen in the effluent results which can for example kill fish even if cyanide present does not.

It is accordingly an object of the invention to seek to mitigate this disadvantage.

According to the invention there is provided apparatus for monitoring impurity in a liquid, comprising a vessel with a plurality of chambers through which the liquid is circulated in use to promote mixing, and a compartment in the vessel in fluid communication with the chambers and adapted to promote a quiescent settlement zone from which liquid is removable.

The plurality of chambers may comprise a series of concentric tubes, or alternatively the interior of the vessel and an internal baffle over which liquid passes to promote mixing.

The vessel may comprise transparent plastic. This provides for visual monitoring of the interior.

There may be an outlet means for liquid from the compartment adapted to remove liquid therefrom intermittently.

The outlet means may comprise a dip tube connected to the inlet of a peristaltic pump adapted to pump at a rate slightly in excess of the feed rate of the fluid to the vessel.

There may be means to circulate fluid from one side of the baffle to the other, which means may include a further peristaltic pump.

There may be a device to measure dissolved oxygen content of the liquid.

The device may comprise a probe adapted to dip into the liquid in the vessel and which is connected to an electronic meter in an electronic control system.

The electrode may include a stirrer, and means to pass a desired flow of air or oxygen to the vessel. The electronic control system may comprise a computer for monitoring the output from the meter and adapted to control the speed of the air or oxygen input means.

According to another aspect, the invention provides an activated sludge sewage treatment plant in combination with apparatus as hereinbefore defined whereof toxicity of the sludge is continuously monitored.

Using the invention it is possible to detect at a sewage works inlet, species of toxin which are toxic to nitrifying bacteria. Such 'early warning' enables the plant Manager(s) to take action to divert the sewage flow to storm tanks while the source of the toxin is identified. The apparatus is thus continuously fed with whole screened sewage from the inlet of the works as a means of detecting toxins. An alarm at this stage in the process provides a time period equivalent to the residence time in primary sedimentation tanks in which to divert the flow to the storm tanks for later disposal.

Apparatus embodying the invention is hereinafter described, by way of example, with reference to the accompanying drawings.

Figure 2:
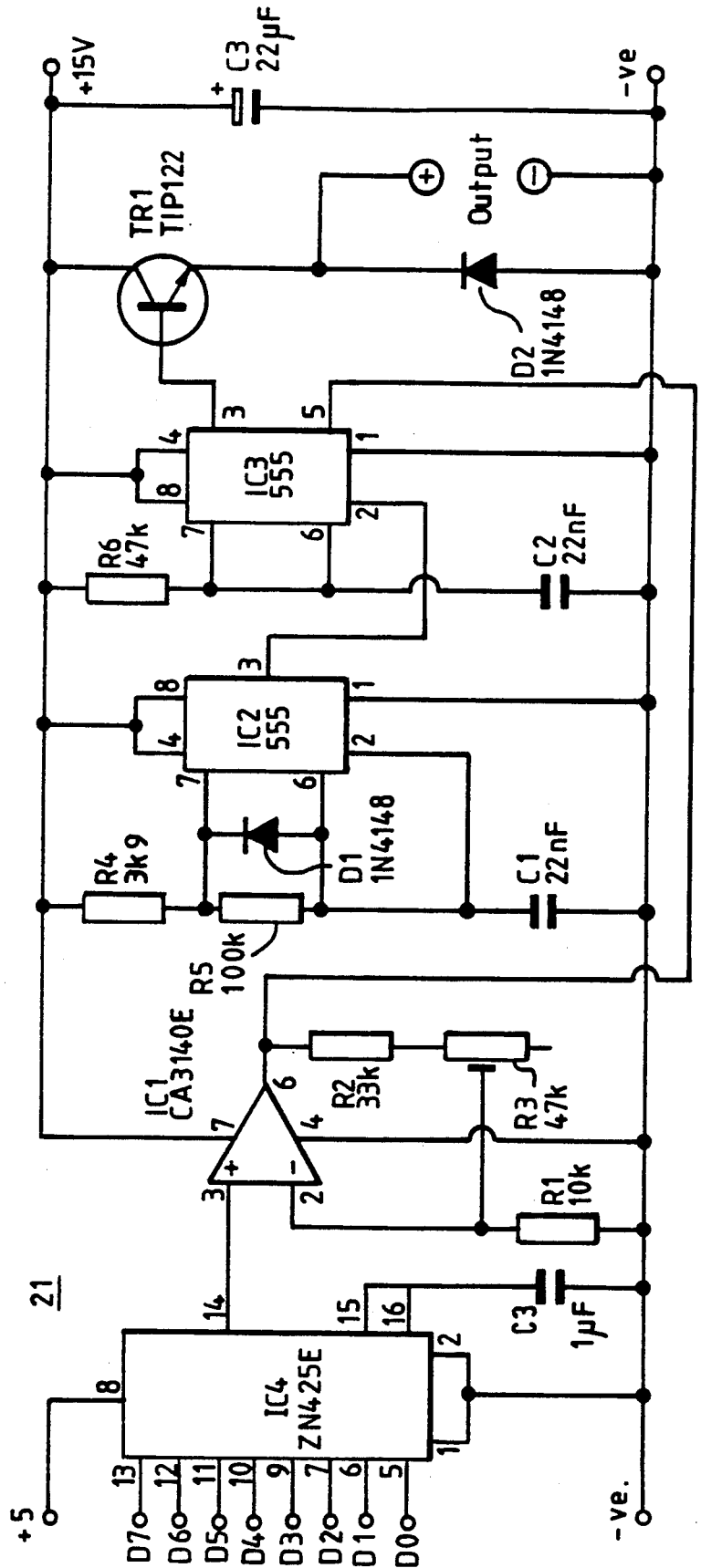

FIG. 1 is a schematic side elevational view of a vessel used in apparatus embodying the invention to monitor the presence of toxins in activated sewage sludge by monitoring the dissolved oxygen level in the sludge; and FIG. 2 is a circuit diagram of a pulsed motor speed controller used in the apparatus.

Referring to the drawings, particularly FIG. 1, there is shown apparatus 2 for monitoring impurity in a liquid, specifically toxin(s) in activated sewage sludge, comprising a vessel 2 with a plurality of chambers 3 and 4 through which the liquid (sludge) is circulated in use to promote mixing, and a compartment 5 in the vessel in fluid communication with the chambers 3 and 4 and adapted to promote a quiescent settlement zone from which liquid is removable.

The vessel 2 is an upright vessel, generally rectangular in plan view made of transparent plastic such as PVC and having an interior upstanding, as viewed, baffle 6 which forms with the interior of the vessel the plurality, in this case two, of chambers 3 and 4. The compartment 5 is a settlement tube 7 which passes through a hole 8 in a lid 9 of the vessel 2, on which it is supported by a flange 10, the length of the tube 7 being over half the height of the vessel 2. The sewage exits the vessel from the tube 7 via an outlet or dip tube 11 connected to a peristaltic pump 12.

The vessel also includes recirculation ports 13 and 14 at the bottom of the chambers one of which 13 comprises an inlet port 15 for the sewage. There is also an inlet means for air/oxygen in the form of an aerator or diffuser 16 also suspended from the lid 9, and extending to near the bottom of the vessel 2 so that air/oxygen can bubble through as great a volume of sewage as possible.

There is further a device 17 for monitoring the dissolved oxygen in the form 18 of a probe which is a meter such as a YSI Model 58 DO Meter equipped with an electrode such as a Clark electrode 19. The electrode 19 has a built in stirrer 20 which enables a better estimate of dissolved oxygen (DO) concentration to be made, while the meter provides a recorder output of 0-1 v DC, which is fed to a DO control system, the rate of supply of air/oxygen to the sludge being controlled by a pulsed DC system under computer control, a circuit 21 for which system is shown in FIG. 2.

There is an additional peristaltic pump for recirculating sludge from one side of the baffle 6 to the other, that is between the chambers 3 and 4 thus providing a degree of 'plug' flow which is more sensitive to poisoning than a system that is completely mixed. In use, sewage is fed to the vessel continuously 'on line' through the inlet 15 and out through the compartment 5. The compartment 5 provides a zone where the mixing velocity approaches zero so that solids can settle. The dip tube 11 barely touches the surface 22 of the effluent in the compartment 5 and the pumping rate of the peristaltic pump is set at such a rate as slightly to exceed the sewage feed rate. In operation, this rapidly provides an equilibrium whereby the tube 11 repeatedly makes and breaks contact with the effluent surface 22 and therefore takes 'sips' of the effluent, which then discharges to waste.

The dissolved oxygen level is kept constant by varying the speed of the aeration pump 16 in response to the dissolved oxygen level recorded. The oxygen demand is, therefore, a function of the aerator speed, where a sudden drop in oxygen demand gives an indication of possible poisoning of the effluent. A smoothing and trend recognition algorithm in the controlling computer's software enables sudden changes in oxygen demand to be isolated, and thus to activate an alarm for diverting the sludge.

The circuit shown in FIG. 2 provides a varying voltage in order to control the speed of the aerators 16. Normally, if voltage were to be varied in response to power demand the result would be poor speed control at low speeds. The system utilized provides a fixed frequency pulse train of DC where the width of the pulses is varied. A short pulse duration results in a small average output voltage, whereas a long pulse width will give a high average output. Thus the aerators receive full power during the period when the pulses are high and this prevents stalling at low speeds.

Referring to FIG. 2, IC2, a 555 timer device, is used in a slightly non standard a stable configuration. The purpose of this part of the circuit 21 is to produce very brief negative trigger pulses for the pulse width modulator. Steering diode D1 has been included so that R5 is bypassed when C1 is discharging, to produce a very short discharge time.

IC3 is used in the standard 555 monostable configuration, and is triggered by applying a negative pulse, from the output of IC2, to the trigger input at pin 2. When IC3 is triggered, the internal transistor which previously placed a short circuit across C2 is switched off. C2 then charges via R6 until the potential reaches two thirds of the supply voltage. The internal transistor then discharges C2, and the positive output pulse from pin 3 of IC3 ends.

The C2 potential at which the output pulse is terminated is set by a potential divider in IC3, but it may be modified by applying a control voltage to pin 5. Effectively, the higher the voltage at pin 5, the longer the output pulses and vice versa. As this particular circuit requires a control voltage range of almost 0 to 15 V, IC1 is used to amplify the 0 to 2.55 V output range of IC4, a ZN425E digital to analog converter. The 8 bit input for IC4 is provided by port A of a 6255 VIA device in the computer. R3 is adjusted to the lowest value that gives full control of the aerator speed.

TR1 is a Darlington transistor capable of providing the current anplification desired for supplying the aerator motors. D2 is fitted to provide the circuit with protection against reverse EMF generated by the motors as each power pulse ends. The computer referred to is suitably controlled by a computer system such as a CAMBRIDGE MICROPROCESSOR SYSTEMS (CMS) 6502 system, which is a rack-mounted machine running a version of BBC BASIC known as Multi-BASIC. The environment provided by Multi-BASIC allows easy access to memory mapped analog and digital I/O cards which plug into the rack. Additionally, software interrupts associated with memory mapped devices are readily set up so that control software need not spend time checking these devices as a 'foreground' task. Apart from the basic 6502 system, 3 additional cards are utilized, namely a 12-bit ADC card, a digital I/O card containing four 6522 versatile interface adaptor (VIA) chips and a graphics display processor card. The VIA board forms the basis of all the digital I/O within the system. A disc drive interface and twin drives provided with the system are used to store scalar factors for the DO signal, together with any other run time information required by the system. The drives are also used to archive oxygen demand data. A standard lv composite video output is provided, which is used to drive an NEC monochrome monitor.

In operation, the DO set point may be selected from the computer keyboard. Any value in the range 2 to 9 mg $l^{-1}$ is allowed. A closed loop system is utilized which samples the DO reading from the YSI meter and compares the reading obtained to the current set point. If the DO deficit or surplus is large enough, the speed of the aerators is changed by a step which is proportional to the deficit or surplus. This proportional change allows the DO to be quickly brought under control without over or under compensation being applied.

Electronic calibration of the YSI meter output against the ADC input in terms of mg $l^{-1}$ DO is carried out by using an automatic scaling algorithm within the software. The algorithm allows for any small offsets and inaccuracies in the output to be taken into account, and stores the scalar factors and user units on disc. This calibration routine need only be carried out once.

The concentration of DO and the corresponding oxygen demand (which is given by the aerator speed) are plotted on screen in the form of 'trend' graphs. The graphs are updated every 30 seconds, which is the interval in which the DO and DO set point are checked. Up to 1 hour of data is displayed on the graphs at any time.

There is an algorithm to identify a sudden downward trend in oxygen demand (signalling inhibition of the microorganisms), whilst not generating false alarms in response to normal trends in demand.

The sewage flowrate is adjusted to a point such that at no time during the day does the aerator speed drop too low for it to be impossible to identify the possibility of inhibition. T his involves adjustment such that complete nitrification never occurs. As the flow rate will be kept constant, the decrease in sewage strength under typical storm conditions also needs to be taken into account when the apparatus 1 is used on site.

On line monitoring of MLSS and automatic solids wastage might be desirable in such a system, but would add greatly to the hardware costs. Therefore, the control of the MLSS concentration will be a manual task. Sampling of the MLSS and calculation of the volume to be withdrawn could be carried out every 2 or 3 days.

In operation too, it is desirable to introduce screened whole sewage into the vessel 2 without continual blocking occurring. Preferably, a two-stage pumping system is utilized, there being a macerating submersible pump providing a high flowrate to a container with baffles which divert residual screenings away from the inlet of the peristaltic pump used to feed the vessel.

We claim:

1. An apparatus for monitoring presence of toxins in activated sewage sludge, comprising:
   (i) a vessel for the sludge;
   (ii) a plurality of chambers in said vessel through which the sludge is circulated sequentially in use to promote mixing of the sludge;
   (iii) an inlet to one chamber of said plurality of chambers for passing the sludge into the vessel;
   (iv) a compartment in one chamber of said plurality of chambers, said compartment being adapted to promote a quiescent settlement zone of the sludge within the vessel whereby solids can settle from the sludge;

(v) an outlet for sludge from said compartment comprising a dip tube which dips into the sludge in the compartment;

(vi) a peristaltic pump operative to withdraw sludge from the compartment through the outlet at a rate slightly in excess of the feed rate of sludge through the inlet to the vessel whereby sludge passes from the quiescent zone through the outlet intermittently in discrete sips; and (vii) a device in one chamber of said plurality of chambers for measuring dissolved oxygen content of the sludge in the vessel.

2. Apparatus according to claim 1, the plurality of chambers comprising the interior of the vessel and an internal baffle over which liquid passes to promote mixing.

3. Apparatus according to claim 2, the vessel comprising transparent plastic.

4. Apparatus according to claim 2, including means to circulate fluid from one side of the baffle to the other.

5. Apparatus according to claim 4, the means including a further peristaltic pump.

6. Apparatus according to claim 1, the device comprising a probe adapted to dip into the liquid in the vessel and connected to an electronic meter in an electronic control system.

7. Apparatus according to claim 6, the probe including a stirrer.

8. Apparatus according to claim 1, including means to pass a desired flow of air or oxygen to the vessel.

9. Apparatus according to claim 8, the electronic control system comprising a computer for monitoring the output from the meter and adapted to control the speed of the air or oxygen input means.

10. An apparatus for aerating sewage sludge, monitoring presence of oxygen and toxins in sewage sludge, and settling solids from sewage sludge, comprising:

(i) a vessel for the sludge;

(ii) a baffle in the vessel dividing the vessel into a pair of chambers;

(iii) means for circulating the sludge through the pair of chambers to promote mixing of the sludge;

(iv) an inlet to a first chamber of said pair of chambers for passing the sludge into the vessel;

(v) a settlement tube extending vertically from a top of the vessel into the sludge in the second chamber of said pair of chambers for forming a compartment within the settlement tube defining a quiescent settlement zone of the sludge within the compartment whereby solids can settle from the sludge;

(vi) an outlet for sludge from said compartment comprising a dip tube which dips into the sludge in the compartment at the desired minimum sludge level;

(vii) a peristaltic pump operative to withdraw sludge from the compartment through the outlet at a rate slightly in excess of the feed rate of sludge through the inlet to the vessel whereby sludge passes from the quiescent zone through the outlet intermittently in discrete sips;

(viii) a device in said first chamber of said pair of chambers for measuring dissolved oxygen content of the sludge in the vessel;

(ix) means for passing a desired flow of oxygen containing gas into the sludge in said first chamber; and (x) an electronic control system responsive to the oxygen measuring device for controlling the oxygen passing means to maintain a set level of dissolved oxygen and for providing a toxin warning upon a sharp rise in measured dissolved oxygen.

* * * * *